US006780644B1

(12) United States Patent
Días et al.

(10) Patent No.: US 6,780,644 B1
(45) Date of Patent: Aug. 24, 2004

(54) USE OF BETA RECOMBINASE IN EUKARYOTIC CELLS, ESPECIALLY FOR TRANSGENIC WORK

(75) Inventors: Vincente Días, Madrid (ES); Fernando Rojo, Madrid (ES); Carlos Martinez Alonso, Madrid (ES); Juan C. Alonso, Madrid (ES); Antonio Bernad, Madrid (ES)

(73) Assignees: Pharmacia Spain S.A., Barcelona (ES); Consejo Superior de Investigaciones Cientificas, Madrid (ES)

( * ) Notice: Subject to any disclaimer, the term of this patent is extended or adjusted under 35 U.S.C. 154(b) by 0 days.

(21) Appl. No.: 09/158,272

(22) Filed: Sep. 22, 1998

Related U.S. Application Data
(60) Provisional application No. 60/062,994, filed on Oct. 23, 1997.

(30) Foreign Application Priority Data

Oct. 8, 1997 (SE) .............................................. 9703663

(51) Int. Cl.[7] .......................... C12N 15/63; C12N 15/87; C12N 15/82; C07H 21/02; C07H 21/04
(52) U.S. Cl. ........................ 435/462; 435/455; 435/468; 435/320.1; 536/23.1; 536/24.3
(58) Field of Search .................... 800/2, 8, 4; 536/23.1, 536/24.33, 24.3; 435/320.1, 325, 183, 91.7, 91.5, 455; 514/2

(56) References Cited

U.S. PATENT DOCUMENTS

| 3,307,330 A | 3/1967 | Niedzielski et al. |
| 4,881,953 A | 11/1989 | Prasad et al. |
| 2002/0123145 A1 * | 9/2002 | Ow .......................... 435/455 |

FOREIGN PATENT DOCUMENTS

| EP | 0 110 858 A1 | 6/1984 | |
| GB | 2 005 152 A | 4/1979 | |
| WO | WO 9640724 | 12/1996 | |
| WO | WO 99/18222 | * 4/1999 | ........... C12N/15/79 |

OTHER PUBLICATIONS

Alsonso et al. Journal of Biological Chemistry 270(7):2938–2945, Feb. 1995.*
Alsonso et al. Molecular Microbiology 18(3):471–478, Nov. 1995.*
Calogero et al. Nature Genetics 22:276–280, Jun. 1999.*
Diaz et al. Journal of Biological Chemistry 274(10):6634–6640, Mar. 1999.*
Hammer et al. Journal of Animal Science 63:269–278, Jul. 1986.*
RF Seamark, Reprod.Fertil. Dev.,Progress and Emerging Problems in Livestock Transgenesis: a Summary Perspective, 1994, vol. 6,No. 5, pp. 653–657.*
RW Moreadith et al., J Mol. Med.,"Gene targeting in embryonic stem cells:the new physiology and metabolism," 1997, 75:208–216.*
RJ Wall et al., J Dairy Sci, "Transgenic Dairy Cattle: Genetic Engineering on a Large Scale," 1997, 80: 2213–2224.*
RE Hammer et al., J Anim. Sci., "Genetic Engineering of Mammalian Embryos," Jul. 1986, 63: 269–278.*
Diaz et al. "New insights into Host Factor . . . " JBC, 276(19):16257–16264, 2001.*
Rojo et al, *Nucleic Acids Research*, 23(16):3181–3188 (1995).
Rojo et al, *J. Mol. Biol.*, 238:159–172 (1994).
WO 0 92 19358, Nov. 12, 1992, International Application Published by WIPO; PCT Application.

* cited by examiner

*Primary Examiner*—Deborah Crouch
*Assistant Examiner*—Joseph Woitach
(74) *Attorney, Agent, or Firm*—Dinsmore & Shohl LLP (57) ABSTRACT

The invention relates to the use of prokaryotic beta recombinase in eukaryotic cells, especially for transgenic work in eukaryotic cells.

It also relates to the use of prokaryotic beta recombinase for site-specific intramolecular recombination between two six sites in eukaryotic cells.

The use of the gene coding for beta recombinase for promoting the deletion of DNA sequences located between directly oriented six sites in mammalian cells and for catalysing site-specific resolution of DNA sequences in an extrachromosomal target introduced into an eukaryotic cell are also disclosed.

41 Claims, 5 Drawing Sheets

USE OF BETA RECOMBINASE IN EUKARYOTIC CELLS, ESPECIALLY FOR TRANSGENIC WORK

The present application claims priority to application Ser. No. 60/062,994, filed Oct. 23, 1997.

The present invention relates to the use of prokaryotic recombinase in eukaryotic cells, especially for transgenic work in eukaryotic cells.

It also relates to the use of prokaryotic beta recombinase for intramolecular recombination in eukaryotic cells and for mediating exclusively intramolecular reactions.

The use of the gene coding for beta recombinase for catalyzing site-specific resolution (deletion) of DNA sequences when the two target sequences (DNA sequences containing six sites) in a plasmid (extrachromosomal target) introduced in the cell by transfection or when the target sequences are integrated in the genome as chromatin associated structures, at several locations is also disclosed.

INTRODUCTION

Several methods have been developed allowing the manipulation of mammalian genomes in order to elucidate the relevance and function of particular genes of interest. Among them, the development of transgenic mouse strains and gene targeting technologies have turned out to be particularly useful (1, 2). These techniques have undergone a new advance with the characterization and application of site-specific recombinases (3).

Site-specific recombinases can be clustered into two major families. The first one (the Int family) comprises those enzymes that catalyze recombination between sites located either in the same DNA molecule (intramolecular recombination leading to resolution or inversion) or in separate DNA molecules (intermolecular recombination leading to integration) (4–7). The later property has been exploited to allow targeted insertion of specific sequences in precise locations (8, 9). The recombinases used for manipulating mammalian genomes are mainly the Cre and the Flp proteins, which belong to the Int family (3). The target sequences for these enzymes, named loxP sites for the Cre enzyme and FRT for Flp, consist on a short inverted repeat to which the protein binds. The recombination process is operative through long distances (up to 70 kb) in the genome. Using these enzymes, several authors have reported site- and tissue-specific DNA recombination in murine models (10–13), chromosomal translocations in plants and animals (14–16) and targeted induction of specific genes (17). For instance, expression of Cre from the lck proximal promoter leads to specific recombination in thymus (10). The gene encoding DNA polymerase beta has been tissue-specifically deleted using the same strategy (11). In a different approach, the SV40 large tumor antigen has been specifically activated in the lenses of mice, resulting in tumours at that location and not in the rest of the animal (18). The Cre-loxP strategy has also been used in combination with inducible promoters, like the case of the interferon gamma inducible promoter, that was used to provoke gene ablation in liver with high efficiency and with less extent in other tissues (12). This powerful site-specific recombination system, however, only allow the induction of a reduced number of recombination event in the same genome. Since each recombination reaction leaves a target sequence for the recombinase in the genome at the crossover site, and because integrases (e.g. Cre and Flp) can catalyze intermolecular recombination, the whole process may lead to undesired chromosomal rearrangements. This general limitation has been proposed to be partially solved by the use of mutant versions of the loxP sequences (18).

The second family of recombinases includes those enzymes that catalyse recombination only when the sites are located in the same DNA molecule (resolution and/or inversion); they are collectively termed resolvases/invertases (19). These site-specific recombinases, which are constrained to intramolecular reactions, could have an advantage over the Int family of recombinases. Beta recombinase, which belongs to the resolvases/invertases family, catalyses exclusively intramolecular deletions and inversions of DNA sequences located between two target sites for the recombinase, termed six (20–22). Each six site comprises 90 bp and is composed by two binding sites for the recombinase, termed I and II (20, 21, see FIG. 1). Beta recombinase is encoded by the beta gene of the Gram-positive-broad-host-range plasmid pSM19035 (22–25).

The earlier known Cre system appears to be limited in the sense that it allows the induction of a reduced number of recombination events within the same mouse genome. When a conditional knockout mouse is made using this system, a loxP site remains in the genome and constitutes a potential target for another recombination event of unknown consequences. This problem would be fully overcome using an exclusively intramolecular site-specific recombinase.

FIGURES

FIG. 1: A and B. Schematic representation of the site specific recombination mechanism mediated by IRAP and the plasmids used.

THE INVENTION

The scope of the invention is defined by the attached claims.

In the example the use of the prokaryotic site-specific beta recombinase for the manipulation of mammalian genomes is explored. The cloning and expression in eukaryotic cells of the gene coding for beta recombinase is described and its ability to catalyse site-specific resolution (deletion) of DNA sequences when the target sequences are either in a plasmid (extrachromosomal target) introduced in the cell by transfection, or integrated in the genome as chromatin associated structures, at several locations is shown. This activity is termed IRAP, for intramolecular recombination activity mediated by the beta protein. By target sequences is meant six site or DNA sequences containing the natural six sites or modified versions that allow recombination activity.

Our results show that beta recombinase is active in an eukaryotic environment, using the machinery/factors provided by the host cell and that beta recombinase can accurately and efficiently catalyse site-specific recombination in mammalian genomes. We show that the prokaryotic beta recombinase can be functionally expressed in eukaryotic cells and can promote the deletion of DNA sequences located between directly oriented target sites (intramolecular recombination activity mediated by the beta protein) in mammalian cells, IRAP. The availability of a tool like IRAP system, that can only catalyse intramolecular site-specific recombination, creates a wide variety of possibilities for the programmed modification of eukaryotic genomes, especially if combined with already-existing methods. For instance, a gene of interest could be engineered in order to have an exon or a group of exons flanked with loxP/FRT and six sites. This would allow the study of gene product influence in two distinct tissues or in the same tissue in different developmental stages, through differential control of Cre/Flp and IRAP expression. Alternatively, two related genes could be inactivated at the same time or at two related stages. The use of inducible promoters would also allow more specific spatio-temporal control of the recombination event.

The possible applications and advantages of this new system is further elaborated under DISCUSSION and CONCLUSION

EXAMPLE 1

Materials and Methods

Plasmids and Cloning

Plasmids pBT233 (23), pBT338 and pCB8 (20) and pLXSN, which carry the resistance marker for G418 (26), have been previously described. The eukaryotic expression vector pSV2 beta globin (27) was kindly provided by Dr. J. Ortin (CNB). The expression plasmid pSV beta was constructed by PCR amplification of the coding sequence for the IRAP from the plasmid pBT233. The primers, SEQ ID NO:1 and SEQ ID NO:2, respectively, used for PCR were:

betaUP
5'-GAGAGAAAGCTTGGTTGGTTGAAAATGGCT-3' (SEQ ID NO: 1) and betaDO
5'-GAGAGATGATCAGTACTCATTAACTATCCC-3' (SEQ ID NO: 2).

These oligonucleotides were engineered to contain HindIII and BclI restriction sites, respectively, which were used to clone the amplified gene in the pSV2 beta globin vector, following standard methods (28). Since BclI is sensitive to methylation, pSV2 beta globin plasmid was isolated from BZ101 (dam$^-$) bacterial strain. The relevant structures are depicted in FIG. 1.

Culture and Cell Lines

Transient expression assays were performed in the simian COS-1 cell line kindly provided by Dr. J. Ortin. Stable clones with the DNA substrate for beta recombinase integrated at different sites of the chromosome were established in the murine cell line NIH/3T3. Both cell lines were grown in Dulbecco's Modified Eagle Medium (DMEM) (Gibco-BRL, Grand Island, N.Y.), supplemented with 10% foetal calf serum (Cultek, Madrid, Spain), 2 mM L-glutamin (Merck, Drmstadt, Germany) and the antibiotics streptomycin (0.1 mg/ml, Sigma, St. Louis, Mo.) and penicillin (100 U/ml, Sigma).

Transfection Conditions and Plasmid DNA Extraction.

The transient expression experiments were performed in COS-1 cells by transfection with DEAE-dextran, as described (28). Cells were harvested 48 h after transfection and the extrachromosomal DNA was extracted using the method described by Hirt (29). In brief, cell pellets were lysed with SDS (Merck) and treated with proteinase K (Boehringer, Mannheim, Germany) at 37° C. The genomic DNA was precipitated with 1 M NaCl (Merck). Upon centrifugation, the supernatant was phenol extracted and plasmid DNA precipitated with ethanol and resuspended in water for further experiments.

Stable cell clones with pCB8 DNA randomly inserted at different genome sites were obtained by electroporation in a Bio-Rad Gene Pulser (Hercules, Calif.) of $2\times10^6$ NIH/3T3 cells at 220 V, 960 mF, with 20 mg of pCB8 DNA and a marker DNA coding for neomycin resistance at a ratio of 10:1. The neomycin resistant cells were selected with 1 mg/ml G418 (Sigma) for approximately two weeks. The stable clones obtained were analyzed in Southern experiments (28) or indirect immunofluorescence, as described.

Immunoblotting and Immunofluorescence

Rabbit polyclonal antibodies against the purified beta recombinase were obtained by conventional techniques (28). Beta recombinase was detected by indirect immunofluorescence or by SDS-PAGE followed by immunoblotting.

Transfected cells were grown on coverstips. After 48 h cells were fixed in methanol:acetone (1:1) at −20° C. for 5 min, air dried and rehydrated with PBS. Cells were then incubated with polyclonal anti-beta recombinase antibodies (1:5000 dilution) at room temperature for 30 min, washed three times for 5 min with PBS and incubated again with a fluorescein conjugated anti IgM antibody (DAKO, Glostrup, Denmark) for 1 h at 37° C. in PBS. The cells were mounted in microscope slides and photographed in a fluorescence microscope.

For immunobloting analysis, transiently transfected cells were harvested 48 h after transfection and lysed in RIPA buffer (137 mM NaCl, 20 mM Tris-HCl pH 8, 1 mM MgCl$_2$, 1 mM CaCl$_2$, 10% glycerol, 1% NP-40, 0.5% sodium deoxicholate, 0.1 % SDS) (Merck). The lysed fraction was separated through SDS-PAGE, blotted onto nitrocellulose membrane (BIORAD), and incubated with polyclonal anti-beta recombinase antibodies, previously blocked with COS-1 total cell lysate (1/500 dilution). Peroxidase-conjugated anti-IgM antibody (DAKO, Glostrup, Denmark) was used as second antibody. Membranes were processed according to the ECL chemiluminescence detection kit (Amersham, UK).

Analysis of Recombination Products

PCR was performed with the GeneAmp PCR System 2400 from Perkin Elmer (Foster City, Calif.), equipped with heating cover. Each reaction was carried out with 0.5 mg of genomic DNA or 1/10 of the Hirt preparation according to supplier's instructions. Taq polymerase (2.5 U) (Perkin Elmer) was added with Perfect Match PCR Enhancer (Stratagene, La Jolla, Calif.) after an initial denaturation (10 min, 94° C.). Thereafter, the procedure (Touch-Down) was as follows: 80° C. 2 min, 5 cycles of denaturation (94° C., 1 min) and annealing/extension at 73° C., 2 min, 5 cycles of 1 min at 94° C. and 2 min at 70° C. This was coupled to 25 cycles of denaturation (94° C., 1 min), annealing (68° C., 30 sec) and extension (72° C., 2 min), and one additional cycle of extension at 72° C. for 5 min. For the PCR analysis of the Hirt preparations we used the 16-mer reverse sequencing primer (#1201) and the 7-mer universal sequencing primer (#1211) from New England Biolabs (Beverly, Mass.).

The primers used for the PCR amplification of the Hirt preparations were unsuitable for the analysis of genomic DNA preparations (low $T_m$). Therefore a new pair of primers, SEQ ID NO:3 and SEQ ID NO:4, respectively, was designed:

pBT338UP158, 5'-CCGGCTCGTATGTTGTGTGGAAT-3' (SEQ ID NO: 3) and pBT338DO802, 5'-TGGCGAAAGGGGGATGTGCTG-3' (SEQ ID NO: 4).

Southern analysis of the PCR products was performed by blotting the DNA separated through agarose gels onto nylon membranes (Amersham). Filters were hybridised at 42° C. in 250 mM phosphate buffer (H 7.2), 50% formamide, 250 mM NaCl, 1 mM EDTA, 7% SDS, and washed in 1×SSC, 0.1% SDS, at room temperature for 30 min, at least twice. The washing temperature was increased when needed. The radioactive labelling of probes was performed with the Prime-It Random Primer Labelling Kit from Stratagene. Nucleotide sequences from the PCR bands of interest were determined by automated fluorescent sequencer and analyzed using Seq-Ed 1.0.3 software (both from Applied Biosystems Inc., Perkin Elmer).

RESULTS

Expression of the Prokaryotic Beta Recombinase in Mammalian Cells.

The coding sequence for beta recombinase was cloned in the pSV2 beta globin vector that directs expression from the SV40 virus early promoter. The resulting construction, pSV beta (FIG. 1B), was transiently transfected in COS-1 cells which express SV40 T-antigen. Under these conditions, the expression by plasmids that contain the early SV40 promoter—included in the pSV beta—is amplyfied. A control plasmid not containing beta recombinase gene, termed pSVc, was also generated.

Figure 2:
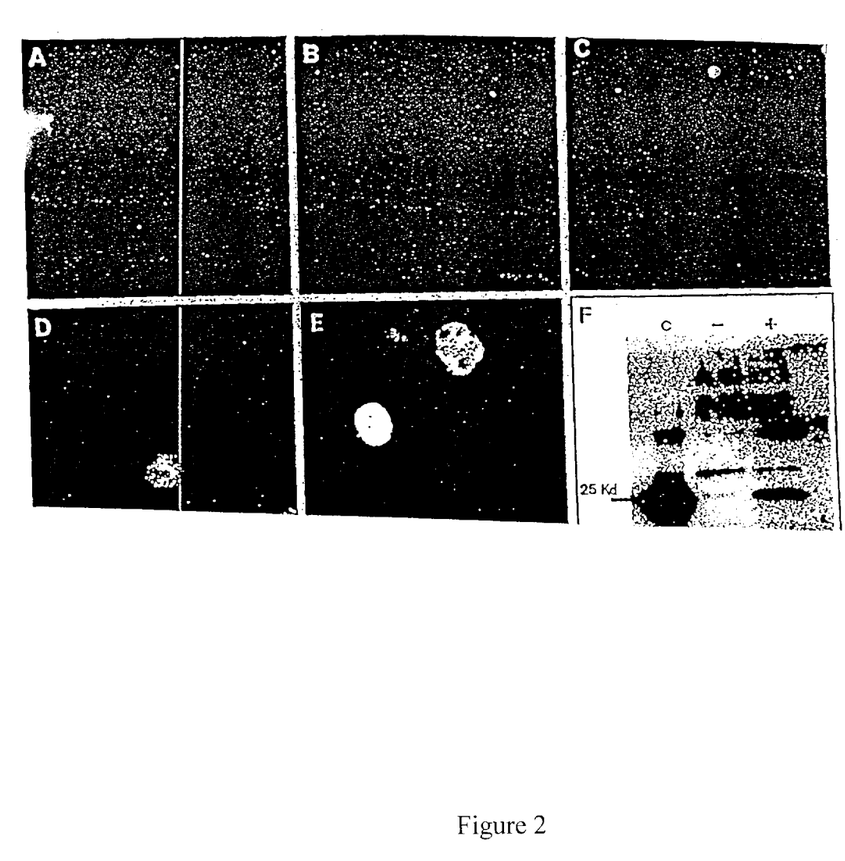
FIGS. 2. A–F. IRAP Expression

Transiently transfected cells were stained with specific antibodies raised against beta recombinase and viewed in a fluorescence microscope. The pSV beta transfected cells showed a strong speckled signal located specifically at the cell nucleus, as it can be seen in FIG. 2, panels D and E. However, very faint staining was detected in the mock and control transfections (FIGS. 2A, B and C). Similar results were obtained when the expression was tested in immunoblot (FIG. 2F). A specific 25 KDa band, corresponding to purified beta protein mobility (c), was developed by the anti-beta recombinase antibodies when COS-1 cells were transfected with the pSV beta plasmid (+) but not in the mock transfected cells (-). These results indicate that beta recombinase can be expressed in eukaryotic environments, showing strong avidity for the nuclear compartment.

Beta Recombinase Catalyzes Site-specific Recombination in Transiently Transfected Mammalian Cells.

Figure 1A:
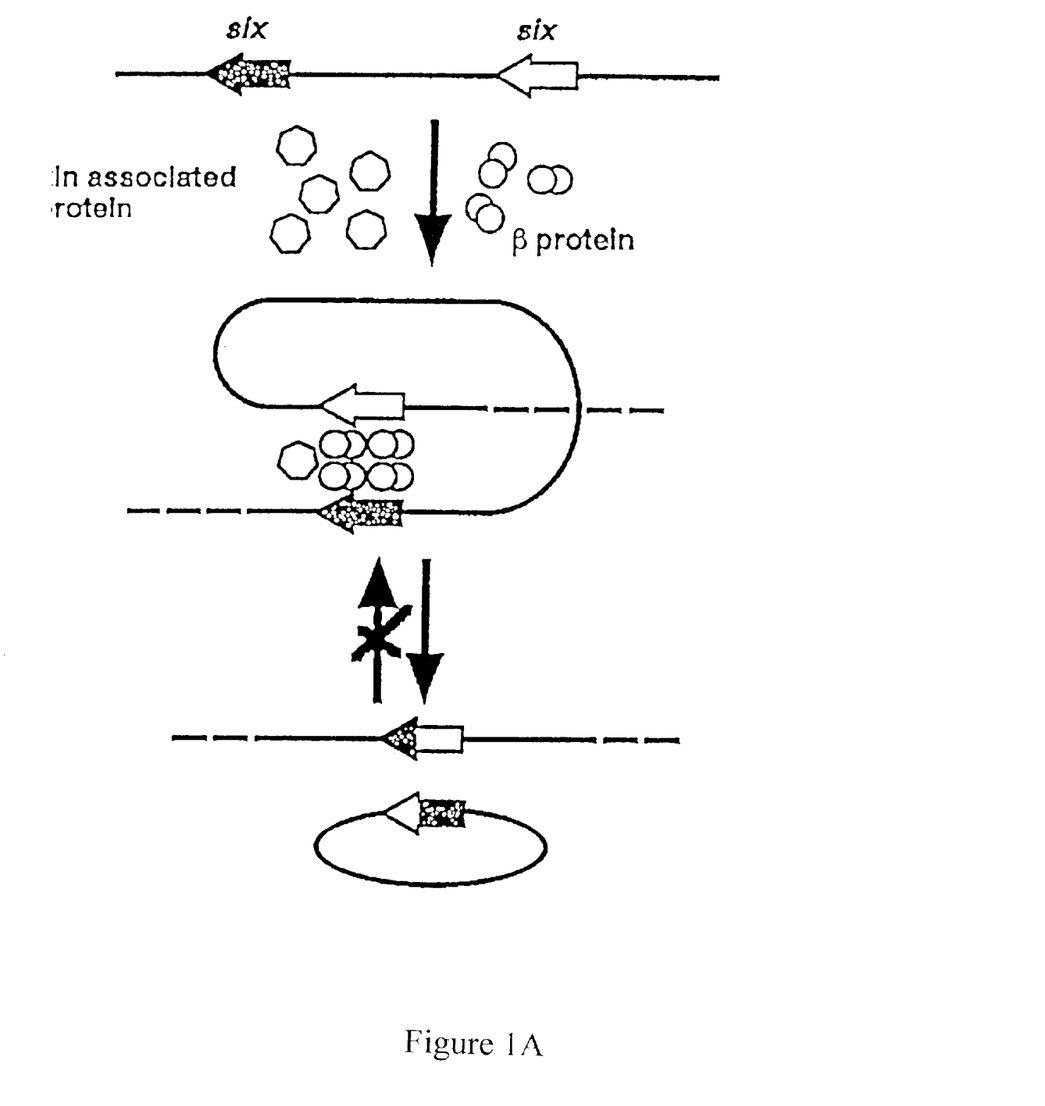

Unlike Integrases with simple recombination sites, such as Cre and Flp, that require no additional protein factors (4, 5, 7), beta recombinase has a strict requirement for a chromatin-associated protein to mediate DNA recombination (20, 22). Beta recombinase binds to the six sites and, with the help of a chromatin-associated protein, promotes strand exchange as depicted in FIG. 1A. Mammalian HMG1/HMG2 chromatin-associated protein can substitute, at least in vitro, for the function of the analogous *B. Subtilis* or *E. coli* proteins , Hbsu and HU respectively (22).

Figure 1B:
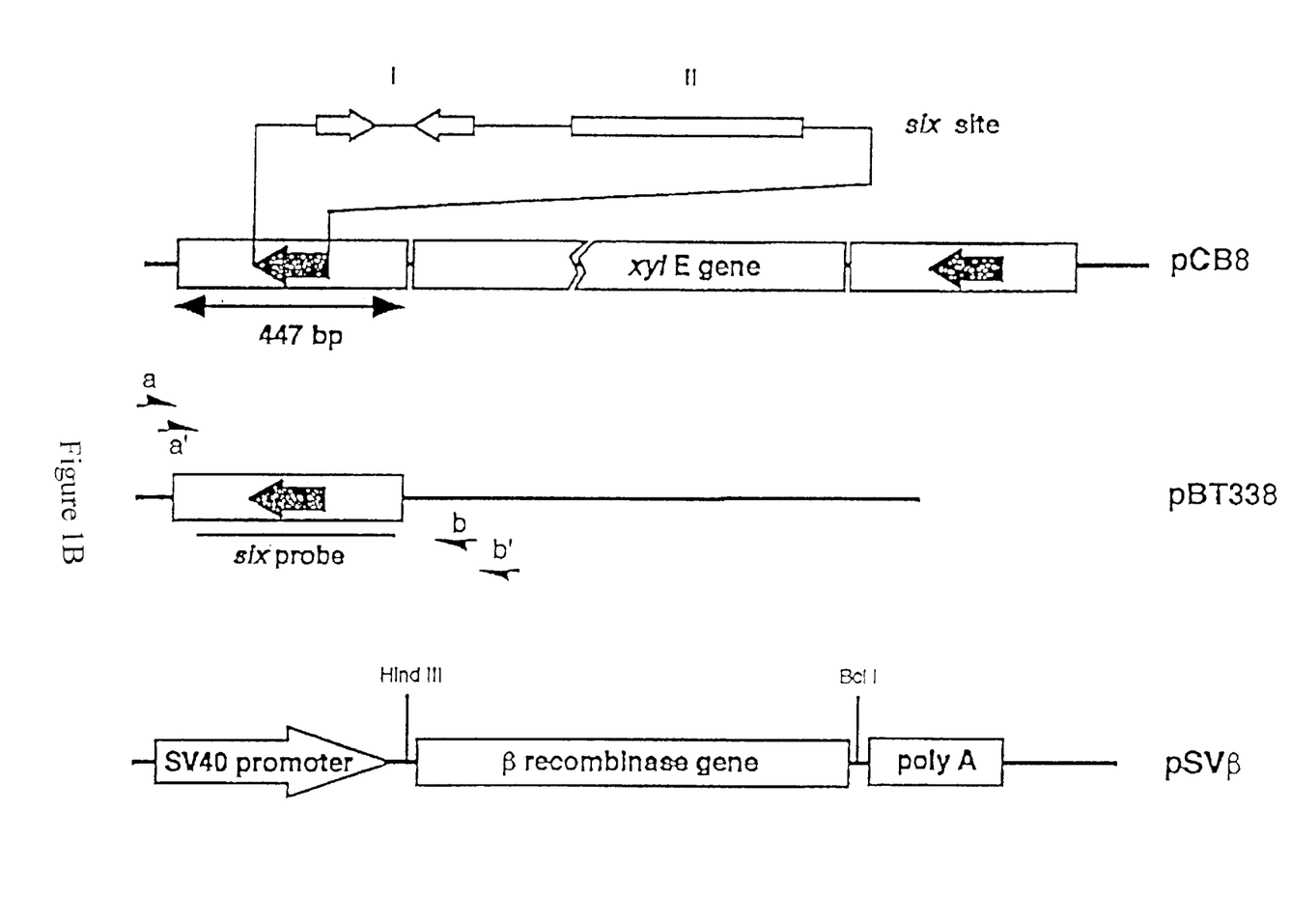

To determine whether eukaryotic cells could account for this host factor, recombination activity due to beta recombinase was first checked by transient co-transfections in COS-1 cells with plasmids pSV beta (bearing the beta recombinase gene) and pCB8 (the substrate DNA containing two target sites for beta recombinase in direct orientation flanking the xylE gene, see FIG. 1B). Upon recombination, a derivative of pCB8 with a single six site should be obtained. The presence of this recombinant product can be easily monitored by PCR amplification of Hirt extracts, using primers complementary to the sequences located upstream of one of the six sites (primer a in FIG. 1B and Materials & Methods), and downstream of the second six site (primer b in FIG. 1B and Materials & Methods). In pCB8, these two primers hybridise to sequences located more than 2.7 Kb apart. Under our PCR conditions this fragment is not efficiently amplified. On the contrary, a 555 bp DNA segment should be amplified from the recombined product. A band of similar length should be obtained when using the same primers and plasmid pBT338 as template, that contains a single six site and was used as positive control (FIG. 1B). Therefore, after transfection of the COS-1 cells (48 h), the extrachromosomal fraction (Hirt extraction) of the cells was purified and the presence of recombination products analyzed by PCR. A clear amplified band of the expected length (555 bp) was observed only when both pCB8 and pSV beta plasmids were co-transfected (see FIG. 3); this band was absent when the two DNAs were transfected separately, or when pCB8 was co-transfected with pSVc, the negative control plasmid. The specificity of the amplified band was further confirmed by Southern hybridization (bottom panel) with a probe specific for the six site (see FIG. 1A). A positive signal of the proper size was detected only in the positive control lane (FIG. 3, pBT338), and in the pCB8/pSV beta co-transfection sample. In lanes corresponding to transfections containing the pSV beta plasmid, the additional band of smaller size detected in the agarose gel was demonstrated to be non-specific, as it did not hybridise to the probe. These results show that beta recombinase is active in an eukaryotic environment, using the machinery/factors provided by the host cell. beta recombinase promotes recombination in chromatin structures.

It has been described the need of supercoiled DNA as a critical condition for beta recombinase mediated deletions (22). To explore whether beta recombinase can promote DNA rearrangements when two six sites form part of the chromatin structure, we established NIH/3T3 cell clones in which the pCB8 construct was integrated at different locations within the mammalian genome. Several stable clones were analyzed by Southern hybridization. Five of them, each one carrying different number of copies (5–75, not shown) of the substrate plasmid, were chosen for transient transfection with the beta recombinase expression plasmid pSV beta. The presence of recombination products was analyzed by PCR of genomic DNA preparations using two primers (pBT338UP158 and pBT338LO802, see Materials and Methods; termed a' and b' respectively in FIG. 1B) that should generate a 668 bp amplified fragment. The amplified DNA fragments were detected by Southern blot assays with a probe specific for the six site. In all cases, a band that hybridised with the probe (aprox. 660 bp) was detected in the pSV beta transfected samples (+) (see FIG. 4). This DNA fragment did not appear when plasmid pSV beta was not included in the transfection (mock transfection, –lanes).

The strength of the signal seemed to correlate with the number of copies of the target construction integrated in the chromosome (not shown), suggesting that recombination had occurred at most of the integrated target sequences. This result also suggests that the recombination efficiency is maintained regardless of the position of the target sequences within the chromatin.

The fidelity of the recombination mechanism was also confirmed by DNA-sequencing of the amplified bands in the case of clones 1 and 2 (data not shown). The regenerated six site (see FIG. 1A) obtained after recombination was unaltered. All together, these data show that beta recombinase can accurately and efficiently catalyse site-specific recombination in mammalian genomes. It seems, therefore, that the chromatin structure provides a superhelical torsion suitable for beta recombinase mediated recombination. Although some of the in vitro futures of beta recombinase activity are not still confirmed in mammalian environments (i.e. inversion, strict intramolecular recombination), we assume that they will be likely maintained in our system. For this reason we define this recombination activity as IRAP for intramolecular recombination activity protein.

DISCUSSION

The common genome manipulation techniques, including transgenesis and gene targeting, have opened a new path to understand a wide variety of mechanisms involving diverse genetic functions. However, the usefulness of these systems becomes limited when the expression or inactivation of a given gene has fatal effects on embryo development, (as an example, see ref. 11, 30) or when the lack of gene function can be bypassed or compensated by redundant mechanisms (31–33). Moreover, the effects of gene inactivation outside the tissue of interest are usually unknown and uncontrollable (34).

These problems have been partially overcome to some extent with the development and application of the site-specific recombination techniques (reviewed in 7) that allow spatio-temporal control of the targeting event. This is the case of the Cre-loxP and Flp-FRP systems (reviewed in 4 and 3). Nevertheless, although the Cre system has proven to be very useful, it seems to be limited in the sense that it allows only a reduced number of recombination event within the same mouse genome. When a conditional knockout mouse is made using this system, a loxP site remains in the genome and constitutes a potential target for another recombination event of unknown consequences. This problem would be overcome if an exclusively intramolecular site-specific recombinase can be used.

In this report we show that the prokaryotic beta recombinase can be functionally expressed in eukaryotic cells and can promote the deletion of DNA sequences located between directly oriented target sites (intramolecular recombination activity mediated by the beta protein) in mammalian cells, IRAP. The protein appears to have high avidity for the nuclear compartment since it was detected after transfection mainly in the nuclear region forming a very condensed and speckled pattern in indirect immunofluorescence. This behavior is similar to that observed for the Cre enzyme (13). Neither Cre nor beta recombinase present in their primary sequence a canonical or bipartite nuclear localization motif (35, 36). Since they have access to the nuclear compartment, we assume that this localization occurs by diffusion through the nuclear membrane or following the transient disorganization of this membrane during mitosis.

Transient expression of IRAP by plasmid pSV beta was able to promote site-specific recombination between the two directly oriented six sites located in the substrate plasmid pCB8 when both plasmids were co-transfected into mammalian cells. As a result, the sequences comprised between the two target sites were deleted from the DNA substrate. The site-specific recombination product was detected by PCR amplification of the Hirt extracts and reassessed by southern hybridization of the amplified products. The presence of this recombination product was strictly dependent on the co-transfection of plasmids pSV beta and pCB8; no recombination products were observed when plasmids pSV beta or pCB8 were transfected separately. It is likely, therefore, that IRAP promotes strand exchange of an extra-chromosomal DNA (pCB8 DNA) in the mammalian environment. Since in vitro recombination requires a chromatin-associated protein (25), we assume that this factor is provided by the host. Indeed, it is known that the mammalian HMG1 chromatin associated protein can efficiently stimulate in vitro beta-mediated recombination (22, 25). We have recently observed that chromatin-associated proteins from plants can also help beta recombinase to mediated DNA recombination (S. Fernandez, K. Grasser, unpublished), suggesting that IRAP could be suitable for manipulation of plant genomes.

We have also investigated the ability of IRAP to act upon chromatin-integrated target substrates. For this, several stable NIH/3T3 clones were established bearing different numbers of copies (5–75) of the substrate plasmid pCB8 randomly integrated in the host chromatin. Transient IRAP expression led to the excision of the sequences comprised between the two directly oriented six sites; the recombination product was detected by PCR amplification from purified genomic DNA and Southern hybridization, and its identity was reassessed by direct DNA sequencing of the amplified product. In these assays, the amount of recombination products seemed to correlate with the copy number of the substrate DNA integrated into the genome, suggesting a high efficiency of recombination and no or low position restriction effects.

The availability of a tool like IRAP system, that can only catalyse intramolecular site-specific recombination, creates a wide variety of possibilities for the programmed modification of eukaryotic genomes, especially if combined with already-existing methods. For instance, a gene of interest could be engineered in order to have an exon or a group of exons flanked with loxP/FRT and six sites. This would allow the study of gene product influence in two distinct tissues or in the same tissue in different developmental stages, through differential control of Cre/Flp and IRAP expression. Alternatively, two related genes could be inactivated at the same time or at two related stages. The use of inducible promoters would also allow more specific spatio-temporal control of the recombination event.

The IRAP system seems to have potential advantages over the already existing methods. Different authors have reported difficulties for the maintenance of loxP sites during the cloning procedures (37), though this seems not to be the case with the six sites. As the six site is larger than the 34-bp loxP site, the existence of potential cryptic sites is less likely, conferring greater target specificity on the recombination reaction. Such cryptic sites have been described for the Cre recombinase (38). Recently, the beta protein target site sequences necessary and sufficient to yield efficient recombination have been narrowed down to a 90 bp DNA segment that includes two recombinase binding sites (sites I and II); the crossing over point is located at the center of site I (39). It is unlikely that a DNA sequence of this size could be present fortuitously in a genome, therefore minimizing the possibilities of accidental chromosome reorganizations at serendipitous sites. In addition, the enzyme seems to have strong avidity for the nucleus, avoiding the need of introducing sequences for nuclear localization (37).

Preliminary results show that constitutive IRAP expression in NIH/3T3 is compatible with normal cell development (not shown). A transgenic mice model for the in vivo expression of the protein is under development. This would demonstrate the in vivo effectiveness of the IRAP-six system for the modification of precise targets.

As stated above, beta recombinase cannot promote intermolecular recombination in vitro or in bacterial cells. Since the potential for generating chromosomal reorganizations would thus be avoided, this tool could be used to promote two or more different specific recombination events at a time in the same animal model regardless of the constitutive expression of IRAP. Thus, the IRAP system offers new possibilities for the development of site-specific genome modifications.

CONCLUSIONS

The development of new strategies for the in vivo modification of eukaryotic genomes has become an important objective of current research. Site-specific recombination has proven useful, as it allows controlled manipulation of murine, plant and yeast genomes. Here we describe that the prokaryotic beta recombinase is active in eukaryotic cells. Beta recombinase has been functionally expressed in eukaryotic cell lines, demonstrating high avidity for the nuclear compartment and forming a clear speckled pattern when assayed by indirect immunofluorescence. In simian COS-1 cells, transient beta recombinase expression promoted deletion of a DNA fragment laying between two directly oriented specific recognition/crossing over sequences (six sites) located as an extrachromosomal DNA substrate. Such intramolecular recombination activity mediated by the beta protein in mammalian cells was termed IRAP. In stable NIH/3T3 clones bearing different copy numbers of the target sequences integrated at distinct chromosome locations. transient IRAP expression also promoted deletion of the intervening DNA, independent of its position and chromatin structure.

FIGURE LEGENDS

FIG. 1. Schematic representation of the site-specific recombination mechanism mediated by IRAP and the plasmids used in this study. (A) The IRAP (shown as a dimer, open circles) interacts, in the presence of a host factor (HMG-1, shown as a monomer, open polygons) with two identical copies of the six site (shaded and open arrows) to form a synaptic complex. This complex is resolved giving rise to a product and a circular intermediate, harboring the intervening sequences, that is finally lost. One full six site remains intact in the host cell. (B) The essential features of plasmid pSVβ and pCB8 and pBT338 DNA are indicated. The six site is shown schematically and sites I and II are highlighted. Orientation of the six sites is denoted by the sense of the shaded arrows. The coding region of the xylE gene, initially designed for expression in bacteria, is indicated. The hybridisation sites of the specific primers a/b and a'/b' pairs used for PCR amplification to detect the recombination products and the probe, used for specific hybridisation controls, are indicated.

FIG. 2. IRAP expression in mammalian cells detected by indirect immunofluorescence and western blot. COS-1 cells, transfected with the indicated plasmids, were grown on glass coverslips. After 48 h, cells were fixed and stained as indicated. Panels A and B correspond to mock- and pSVc-transfected cells, respectively, incubated first with anti-β recombinase polyclonal antibodies and developed with fluorescein-conjugated anti-rabbit IgG. Panels C, D and E show pSVβ-transfected cells. In panel C, the pSVβ-transfected cells were incubated first with preimmune rabbit serum, then developed as above. In panels D and E, showing two different fields of the pSVβ-transfected cells, they were incubated with polyclonal anti-β recombinase antibodies and developed as above. Panel F. COS-1 cells, transfected as indicated, were harvested after 48 h and lysed as indicated in Materials & Methods. The whole cell extract proteins were resolved by SDS-PAGE, blotted onto nitrocellulose and analysed by western blot. The figure shows the autoradiography of a western blot incubated first with polyclonal anti-β recombinase antibodies and developed with peroxidase-conjugated anti-IgM. C, purified β recombinase protein (10 ng); −, mock-transfected COS-1 cells; and +, pSVβ-transfected COS-1 cells. The molecular mass of the band of interest is indicated.

Figure 3:
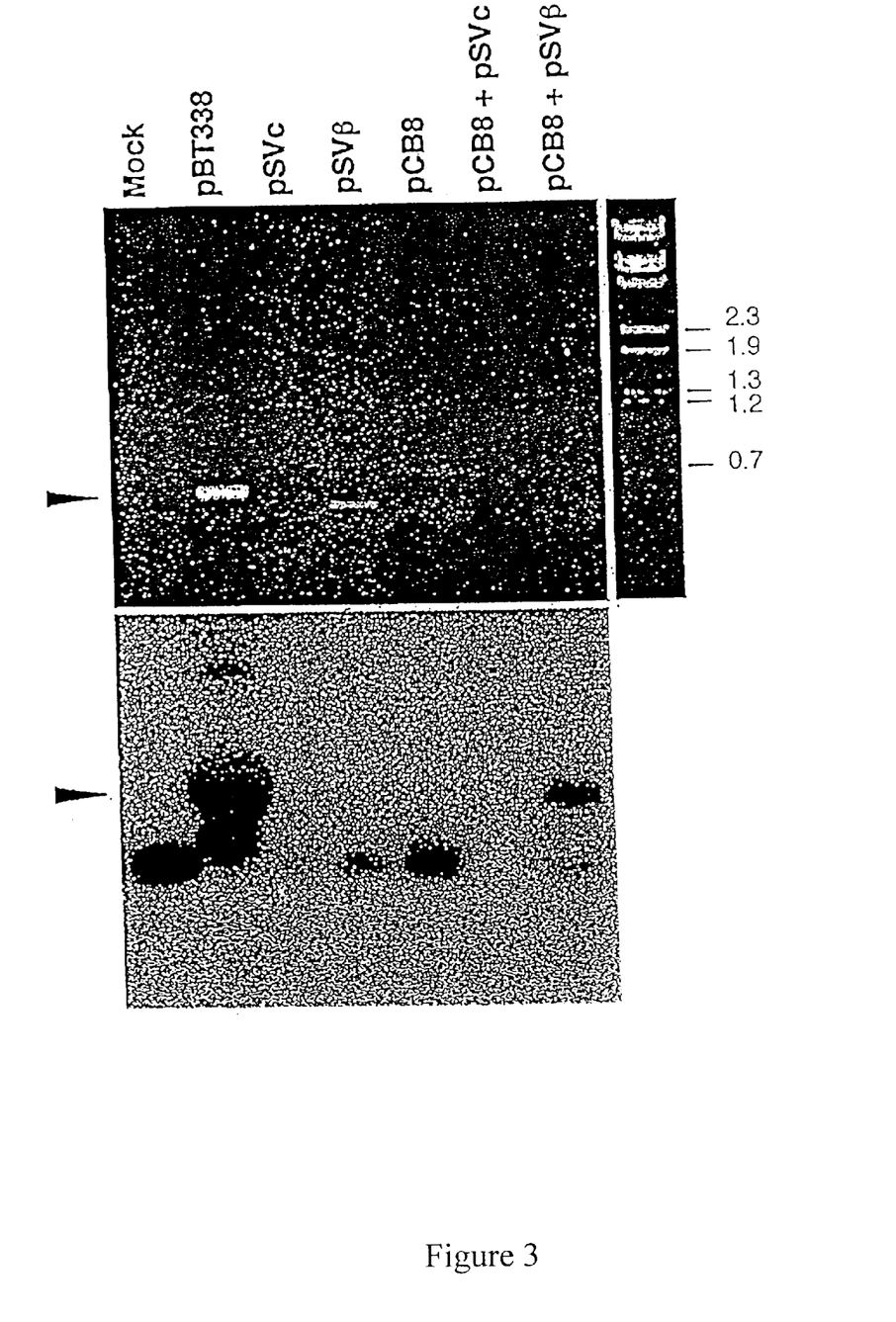
FIG. 3. Functional expression of IRAP

FIG. 3. Functional expression of IRAP assessed in transient transfection experiments. COS-1 cells were transfected with the indicated combinations of plasmids: pCB8, pSVβ, pSVc, pSVc+pCB8 and pSVβ+pCB8. Hirt extracts were obtained 48 h after transfection. The upper panel shows the result of PCR amplification from the Hirt extracts using the primer a/b pair indicated in FIG. 1B. Mock lane shows the negative controls of the PCR amplification, and lane pBT338 shows the positive control (100 pg of plasmid). The size marker lane corresponds to BstEII-digested lambda DNA (500 ng). The lower panel shows the southern blot analysis of the agarose gel presented in the upper panel using a specific probe for the six site (see FIG. 1B). The position of the band of interest is highlighted.

Figure 4:
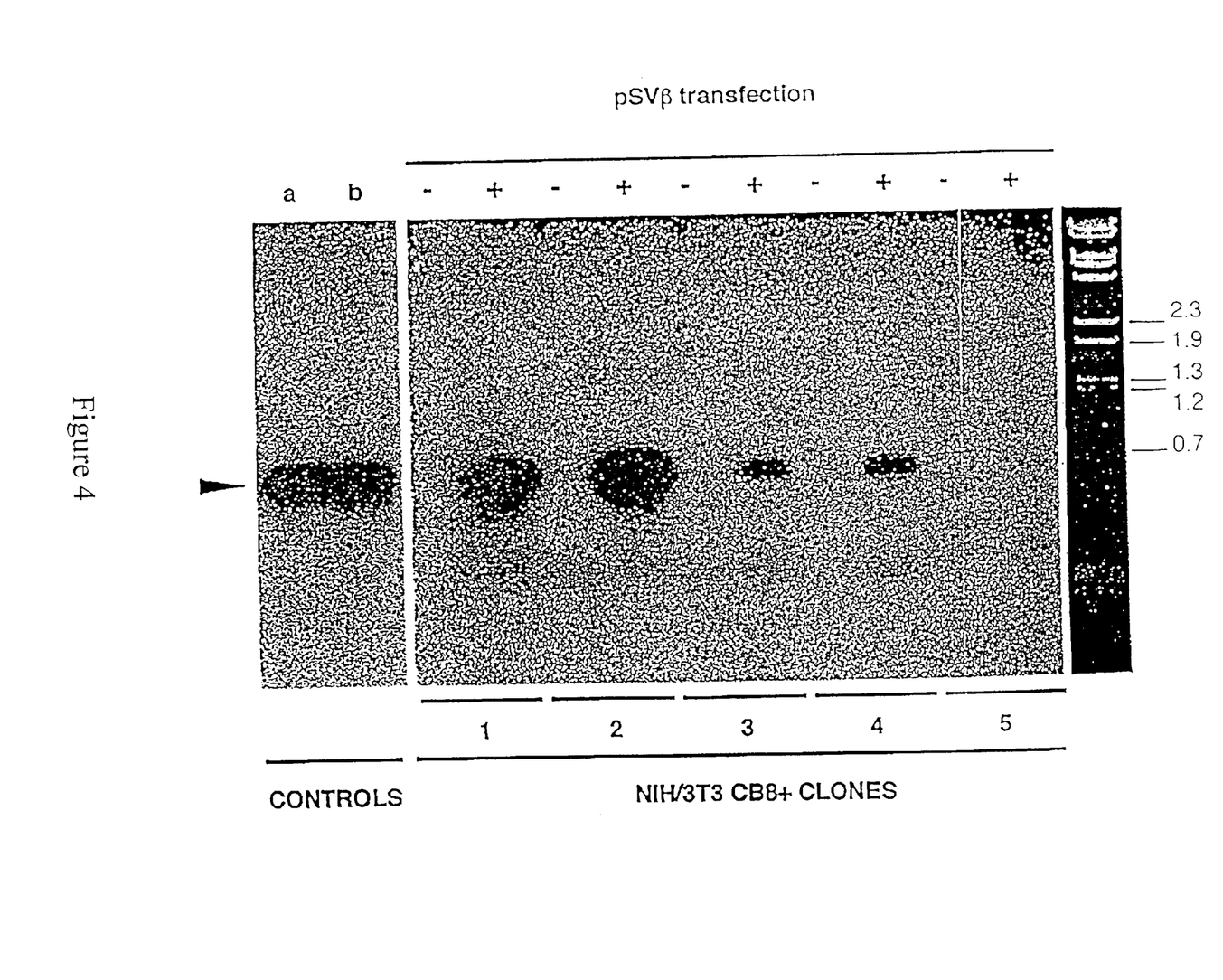
FIG. 4. IRAP-mediated site specific recombination.

FIG. 4. IRAP-mediated site-specific recombination in chromatin-associated targets. Five NIH/3T3 clones (1–5) harboring several copies (approx. 75, 72, 12, 18 and 5, respectively) of pCB8 DNA integrated in different chrosomal locations were isolated and characterized. These clones were transiently transfected, either with (+) or without (−) plasmid pSVβ. Genomic DNA was purified 48 h after transfection and 500 ng of each sample were analyzed by PCR in the conditions described using the primer a'/b' pair (see FIG. 1B). One tenth of each sample was electrophoresed in 0.8% agarose gel, blotted onto nylon membrane and hybridised with an appropriate probe. Controls: (a) pBT338 (100 pg) and (b) pBT338 (100 pg+500 ng of NIH/3T3 genomic DNA). The size marker corresponds to BstEII-digested lambda DNA (500 ng). The size (0.66 kb) and position of the band of interest is indicated.

REFERENCES

1. Brandon, E. P., Idzerda, R. L. and McKnight, G. S. (1995) Curr Biol, 5, 625–34.
2. Brandon, E. P., Idzerda, R. L. and McKnight, G. S. (1995) Curr Biol, 5, 758–65.
3. Kilby, N. J., Snaith, M. R. and Murray, J. A. (1993) Trends Genet, 9,413–21.
4. Sauer, B. (1993) Methods Enzymol, 225, 890–900.
5. Dymecki, S. M. (1996) Proc Natl Acad Sci USA, 93, 6191–6.
6. Abremski, K. and Hoess, R. (1984) J Biol Chem, 259, 1509–14.
7. Nash, H. A. (1996) in Escherichia coli and Salmonella cellular and molecular biology., ed. F. C. Neidhart, R. I. Curtis, J. L. Ingraham, E. C. C. Lin, K. B. Low, B. Magasanik, W. S. Rezaikoff, M. Riley, M. Schaechter and H. E. Umbager (A. S. M. Press, Washington D.C.), pp. 2363–76.
8. Sauer, B. and Henderson, N. (1990) The New Biologist, 2, 441–9.
9. Fukushige, S. and Sauer, B. (1992) Proc. Natl. Acad. Sci. USA, 89, 7905–9.
10. DiSanto, J. P., Muller, W., Guy, G. D., Fischer, A. and Rajewsky, K. (1995) Proc Natl Acad Sci USA, 92, 377–81.
11. Gu, H., Marth, J. D., Orban, P. C., Mossmann, H. and Rajewsky, K. (1994) Science, 265, 103–6.
12. Kuhn, R., Schwenk, F., Aguet, M. and Rajewsky, K. (1995) Science, 269, 1427–9.
13. Orban, P. C., Chui, D. and Marth, J. D. (1992) Proc. Natl. Acad. Sci. USA, 89, 6861–5.

14. Deursen, J. v., Fornerod, M., Rees, B. v. and Grosveld, G. (1995) *Proc. Natl. Acad. Sci. USA*, 92, 7376–80.
15. Medberry, S. L., Dale, E., Qin, M. and Ow, D. W. (1995) *Nucleic Acids Res*, 23, 485–90.
16. Osborne, B. I., Wirtz, U. and Baker, B. (1995) *Plant J*, 7, 687–701.
17. Pichel, J. G., Lakso, M. and Westphal, H. (1993) *Oncogene*, 8, 3333–42.
18. Sauer, B. (1996) *Nucleic Acids Res.* 24, 4608–13.
19. Grindley, N. D. F. (1994) in *Nucleic Acids and Molecular Biology*, ed. F. Eckstein and D. M. J. Lilley (Springer-Verlag, Berlin), pp. 236–67.
20. Rojo, F. and Alonso, J. C. (1994) *J Mol Biol*, 238, 159–72.
21. Rojo, F. and Alonso, J. C. (1995) *Nucleic Acids Res*, 23, 3181–8.
22. Alonso, J. C., Weise, F. and Rojo, F. (1995) *J Biol Chem*, 270, 2938–45.
23. Ceglowsky, P., Boitsov, A., Chai, S. and Alonso, J. C. (1993) *Gene*, 136, 1–12.
24. Rojo, F., Weise, F. and Alonso, J. C. (1993) *Febs Lett*, 328, 169–73.
25. Alonso, J. C., Gutiérrez, C. and Rojo, F. (1995) *Mol Microbiol*, 18, 471–8.
26. Miller, A. D. and Rossman, G. J. (1989) *Biotechniques*, 7, 980–90.
27. Mulligan, R. C., Howard, B. H. and Berg, P. (1979) *Nature*, 277, 108–14.
28. Maniatis, T., Frisch, E. F. and Sambrook, J. (1982) *Molecular Cloning: A Laboratory Manual* (Cold Spring Harbor Lab., Cold Spring Harbor, N.Y.), pp.
29. Hirt, B. (1967) *J Mol Biol*, 26, 365–9.
30. Ioffe, E. and Stanley, P. (1994) *Proc Natl Acad Sci USA*, 91, 728–32.
31. Schorle, H., Holtschke, T., Hunig, T., Schimpl, A. and Horak, I. (1991) *Nature,* 352, 621–4.
32. Kühn, R., Rajewsky, K. and Müller, W. (1991) *Science*, 254, 707–10.
33. Kopf, M., Lamers, M., Bluethman, M. and Kohler, G. (1994) *Nature*, 376, 339–45.
34. Dranoff, G., Crawford, A. D., Sadelain, M., Ream, B., Rashid, A., Bronson, R. T., Dickersin, G. R., Bachurski, C. J., Mark, E. L., Whiisett, J. A. and Mulligan, R. C. (1994) *Science*, 264, 713–6.
35. Nath, S. T. and Nayak, D. P. (1990) *Mol Cel Biol*, 10, 413945.
36. Robbins, J., Dilworth, S. M., Laskey, R. A. and Dingwall, C. (1991) *Cell*, 64, 615–23.
37. Bergemann, J., Kuhlcke, K., Fehse, B., Ratz, I., Ostertag, W. and Lother, H. (1995) *Nucleic Acids Res*, 23, 4451–6.
38. Sauer, B. (1992) *J. Mol. Biol.*, 223, 911–28.
39. Canosa, I., Rojo, F. and Alonso, J. C. (1996) *Nucleic Acids Res*, 24, 2712–7.

What is claimed is:

1. A method for mediating recombination between two six sites, in in vitro cells, comprising the steps of transfecting the cells with prokaryotic beta recombinase derived from Streptococcus and transfecting the cells with DNA sequences containing six sites that allow recombination activity; wherein recombination occurs between two six sites.

2. A method according to claim 1, wherein two or more intramolecular recombination events involving different DNA sequences located between different six sites occur at the same time.

3. A method according to claim 1, wherein an intramolecular deletion of DNA sequences located between directly oriented six sites is obtained.

4. A method according to claim 3, wherein the DNA sequences are located within an extrachromosomal DNA substrate.

5. A method according to claim 4, wherein the extrachromosomal DNA substrate is a plasmid.

6. A method according to claim 1, wherein an intramolecular inversion of DNA sequences located between inverted repeated six sites is obtained.

7. A method according to claim 6, wherein the DNA sequences are located within an extrachromosomal DNA substrate.

8. A method according to claim 7, wherein the extrachromosomal DNA substrate is a plasmid.

9. A method according to claim 1, wherein an intramolecular deletion of a DNA sequence located between directly oriented six sites is obtained.

10. A method according to claim 1, wherein an intramolecular inversion of a DNA sequence located between two inversely oriented six sites is obtained.

11. A method according to claim 1, wherein the cells comprise eukaryotic cells.

12. A method according to claim 1, wherein the cells comprise mammalian cells.

13. A method for mediating recombination between two six sites, in in vitro cells, comprising the steps of transfecting the cells with prokaryotic beta recombinase derived from Streptococcus and integrating DNA sequences containing six sites that allow recombination activity into chromatin of the cells; wherein recombination occurs between two six sites.

14. A method according to claim 13, wherein an intramolecular deletion of DNA sequences located between direct repeated six sites is obtained.

15. A method according to claim 13, wherein an intramolecular inversion of DNA sequences located between inverted repeated six sites is obtained.

16. A method according to claim 13, wherein the cells comprise eukaryotic cells.

17. A method according to claim 13, wherein the cells comprise mammalian cells.

18. A method for mediating recombination between two six sites, in in vitro cells, comprising the steps of transfecting the cells with prokaryotic beta recombinase derived from Streptococcus and transfecting the cells with DNA sequences containing six sites that allow recombination activity; wherein an intramolecular deletion of a DNA sequence located between direct repeated DNA sequences containing six sites is obtained.

19. A method according to claim 18, wherein the cells comprise eukaryotic cells.

20. A method according to claim 18, wherein the cells comprise mammalian cells.

21. A method for mediating recombination between two six sites, in in vitro cells, comprising the steps of transfecting the cells with prokaryotic beta recombinase derived from Streptococcus and transfecting the cells with DNA sequences containing six sites that allow recombination activity; wherein an intramolecular inversion of a DNA sequence located between inverted repeated DNA sequences containing six sites is obtained.

22. A method according to claim 21, wherein the cells comprise eukaryotic cells.

23. A method according to claim 21, wherein the cells comprise mammalian cells.

24. A method for catalyzing site-specific resolution of DNA sequences located between six sites in an extrachromosomal substrate transfected into an in vitro cell, comprising the step of catalyzing the site-specific resolution with prokaryotic beta recombinase derived from Streptococcus; wherein recombination occurs between six sites.

25. A method according to claim 24, wherein the resolution is deletion.

26. A method according to claim 24, wherein the resolution is inversion.

27. A method according to claim 24, wherein the extrachromosomal substrate is a plasmid.

28. A method according to claim 24, wherein the cells comprise mammalian cells.

29. A method according to claim 24, wherein the cells comprise eukaryotic cells.

30. A method for mediating recombination in in vitro cells, comprising the steps of transfecting the cells with prokaryotic beta recombinase derived from Streptococcus and transfecting the cells with DNA sequences containing six sites that allow recombination activity; wherein recombination occurs between six sites and in the presence of cell factors comprising HMG1 chromatin-associated protein.

31. A method according to claim 30, wherein the cells comprise eukaryotic cells.

32. A method according to claim 30, wherein the cells comprise mammalian cells.

33. A method for mediating recombination in chromatin structures, comprising the steps of transfecting in vitro cells with prokaryotic beta recombinase derived from Streptococcus and integrating DNA sequences containing six sites that allow recombination activity into chromatin of the cells; wherein recombination occurs between six sites and in the presence of cell factors comprising HMG1 chromatin-associated protein.

34. A method according to claim 33, wherein the cells comprise eukaryotic cells.

35. A method according to claim 33, wherein the cells comprise mammalian cells.

36. A method for catalyzing site-specific resolution of DNA sequences located between six sites which are integrated into chromatin of an in vitro cell, comprising the step of catalyzing the site-specific resolution with prokaryotic beta recombinase derived from Streptococcus; wherein recombination occurs between six sites.

37. A method according to claim 36, wherein the six sites are wrapped on a nucleosome at several locations.

38. A method according to claim 36, wherein the cells comprise eukaryotic cells.

39. A method according to claim 36, wherein the cells comprise mammalian cells.

40. A method for mediating recombination between two six sites, in mouse cells, comprising the steps of transfecting mouse cells with prokaryotic beta recombinase derived from Streptococcus and transfecting the mouse cells with DNA sequences containing six sites that allow recombination activity; wherein recombination occurs between two six sites.

41. A method for mediating recombination between two six sites, in mouse cells, comprising the steps of transfecting mouse cells with prokaryotic beta recombinase derived from Streptococcus and integrating DNA sequences containing six sites that allow recombination activity into chromatin of the mouse cells; wherein recombination occurs between two six sites.

* * * * *

UNITED STATES PATENT AND TRADEMARK OFFICE
CERTIFICATE OF CORRECTION

PATENT NO. : 6,780,644 B1
DATED : August 24, 2004
INVENTOR(S) : Vincente Dias et al.

It is certified that error appears in the above-identified patent and that said Letters Patent is hereby corrected as shown below:

Column 13,
Line 30, change "between" to -- between two --.

Column 14,
Line 57, change "between" to -- between two --.

Signed and Sealed this

Twenty-fifth Day of January, 2005

JON W. DUDAS
*Director of the United States Patent and Trademark Office*

SEQUENCE LISTING

```
<160> NUMBER OF SEQ ID NOS: 4

<210> SEQ ID NO 1
<211> LENGTH: 30
<212> TYPE: DNA
<213> ORGANISM: plasmid psV beta - betaUP primer

<400> SEQUENCE: 1
gagagaaagc ttggttggtt gaaaatggct                                        30

<210> SEQ ID NO 2
<211> LENGTH: 30
<212> TYPE: DNA
<213> ORGANISM: plasmid psV beta - betaUP primer

<400> SEQUENCE: 2
gagagatgat cagtactcat taactatccc                                        30

<210> SEQ ID NO 3
<211> LENGTH: 23
<212> TYPE: DNA
<213> ORGANISM: pBT338UP158 primer

<400> SEQUENCE: 3
ccggctcgta tgttgtgtgg aat                                               23

<210> SEQ ID NO 4
<211> LENGTH: 21
<212> TYPE: DNA
<213> ORGANISM: pBT338DO802 primer

<400> SEQUENCE: 4
tggcgaaagg gggatgtgct g                                                 21
```